United States Patent [19]

Rybicki

[11] 4,413,891
[45] * Nov. 8, 1983

[54] REFRACTOR OPTICAL SYSTEM

[75] Inventor: Edward B. Rybicki, Depew, N.Y.

[73] Assignee: Warner Lambert Technologies, Inc., Southbridge, Mass.

[*] Notice: The portion of the term of this patent subsequent to Aug. 5, 1997 has been disclaimed.

[21] Appl. No.: 134,374

[22] Filed: Mar. 27, 1980

Related U.S. Application Data

[63] Continuation-in-part of Ser. No. 894,455, Apr. 7, 1978, Pat. No. 4,215,919.

[51] Int. Cl.³ .................................................. A61B 3/02
[52] U.S. Cl. .................................................. 351/235
[58] Field of Search .................. 351/10, 11, 12, 19, 351/20, 21, 22, 27, 28, 29

[56] References Cited

U.S. PATENT DOCUMENTS 1,455,457  5/1923  Tillyer.
2,266,797  12/1941  Peck et al..

OTHER PUBLICATIONS

Lang et al, Additive Lens Systems in Eye Refractors, American Journal of Optometry & Physiological Optics, 8/75, pp. 533–540.

Primary Examiner—John K. Corbin
Assistant Examiner—Rodney B. Bovernick
Attorney, Agent, or Firm—Alan H. Spencer

[57] ABSTRACT

A refractor optical system having a new series of spherical and cylinder lenses substantially eliminates the irregular occurrence of additive errors when lenses spaced from the reference plane are used or more than two lenses are combined and permits correction for the significant additive errors by non-additive lens selection is disclosed.

3 Claims, 1 Drawing Figure

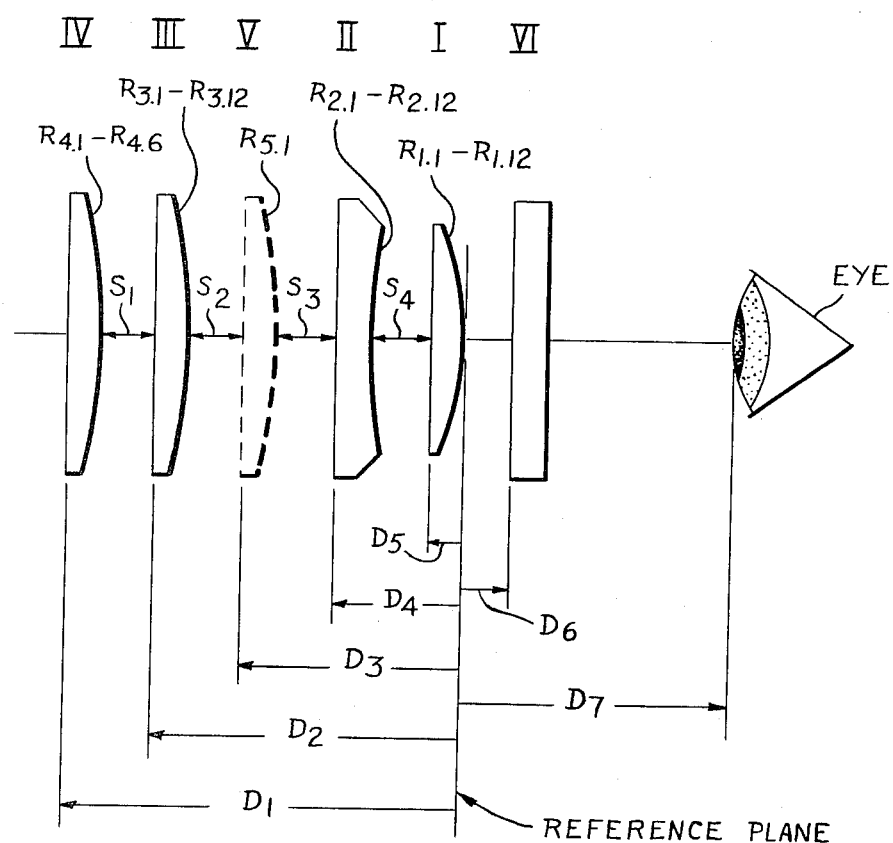

REFRACTOR OPTICAL SYSTEM

BACKGROUND OF THE INVENTION

This is a continuation-in-part of application Ser. No. 894,455, filed Apr. 7, 1978, now U.S. Pat. No. 4,215,919.

This invention relates to refractor optical systems and, more particularly, to a spherical and a cylinderical lens series for a refractor having regular additive errors to permit non-additive combinations for correction of additive error.

Refractors are well known ophthalmic instruments used for determining the proper lens value necessary to correct the defective vision of a patient. The refractor typically includes a right hand battery and a left hand battery, each for enabling the practitioner to place various corrective lenses in alignment with a respective patient's eye. Each of the batteries is alike and each includes a series of spherical lenses and series of cylindrical lenses. The spherical lens assembly and the cylindrical lens assembly each conventionally include a pair of discs. One of each pair of discs contains lenses having a "weak" power in incremental increases of power and the other disc of each pair contains lenses having "strong" power. The lenses of the "strong" power disc are of sequentially increasing power with the increments of increasing power usually at least being equal to the highest power of the corresponding "weak" lens plus the "weak" lens increment. The practitioner may rotate one of the lenses in each disc into alignment with the patient's eye. In early refractors, like trial lens sets, the practitioner could select the particular combination of lenses which he wished to place before the patient's eyes. Each lens was manufactured to have a specific power whether the lens was used by itself or in combination with one or more other lenses. For example, to provide a cylinder power of plus 6.50 diopters, the practitioner would select the +6.0 diopter sphere lens and the +0.5 diopter cylinder lens. In lens series of such prior art devices, the designer attempted to minimize the error in any particular combination since each lens, for example, the +0.25 diopter cylinder lens, was used any time the practitioner needed to add 0.25 diopter of cylinder. In the average trial lens sets, there are over three thousand lens combinations in which the 0.25 diopter cylinder lens may be used. Since the only way to correct for additive error was to refer to a reference chart which covered all the permutations of lens combinations, the lens designer attempted to minimize the error resulting from combining lenses in each possible combination of the series.

As used hereinafter, the term "additive error" refers to the difference between the real cylinder power of a lens combination and the power expected from the sum of the powers of the individual cylinder lenses in the combination. The term "significant" additive error is used herein to denote additive error in excess of 0.1 diopter.

As refractors developed and became more refined, the disc containing the "weak" lenses were mechanically coupled to the disc containing the "strong" lenses. This permitted the practitioner to operate a single control to vary the spherical power presented to the eye and similarly a single control to vary the cylinder power presented to the eye. The constrictions placed upon lens design were even more severe in such instruments because the mechanical linkage used to couple the cylinder lens discs prevents the practitioner from personally selecting individual lens combinations.

PRIOR ART

U.S. Pat. No. 1,455,457, issued May 15, 1923 to Tillyer, discloses a "new" series of test lenses which minimizes additive error when more than one lens is used. This patent describes the defects of the prior art and teaches that the minimization of the amount of error when combining lenses is important. The lens series is not designed to provide the least number of errors or predictable combinations which have significant error.

U.S. Pat. No. 2,266,797, issued Dec. 23, 1941 to Peck et al, discloses an early refractor in which lenses in the "weak" lens disc were not mechanically coupled to lenses in the "strong" lens disc. The patent further discloses the manner in which the various lens power in individual discs are combined to provide the resultant power desired by the practitioner. Although one object of the described invention is to provide a "cooperatively functioning series of lenses computed as to curvatures and thicknesses, distance between lenses of said series and position of said lenses before the eye", the patent contains no description of the lens series by or means for determining the lens series. *AMERICAN JOURNAL OF OPTOMETRY AND PHYSIOLOGICAL OPTICS*, Volume 52, Pages 533-540 (August, 1975) presents a reprint of a paper read at the American Academy of Optometry Annual Meeting in December of 1974, entitled *Additive Lens Systems in Eye Refractors*. The paper evaluates the lens series of the 1923 Tillyer patent and establishes that the series is correct for only two lenses in combination. The paper further points out that additional lenses can cause additive error in excess of 0.5 diopter. In conclusion, the paper finds that a programmable desk top calculator, a computer actuated eye refractor, or a micro computer are required to present a plurality of lenses without additive error or convert the lenses actually presented to real power when printing out the prescription.

It is an object of the present invention to overcome the deficiencies and inadequacies of the prior art.

It is another object of the present invention to provide a lens series for use in a refractor having predictable combinations of lenses which produce significant additive error.

It is still another object of the present invention to provide a lens series in which additive error of every combination of cylinder lenses is identical for all lenses of the strong sphere dial including the zero power plate.

BRIEF DESCRIPTION OF THE INVENTION AND DRAWINGS

A refractor singlet lens series, where all lenses presented at the reference plane (called the A lenses) have the same glass or plastic, the same thickness, one surface having the same radius and the same spacings to the next combined lens, will not change the additive error for a combination of three or more lenses when the A lens of the combination is changed. It is understood that, if the series of A lenses contains a zero power position, this position must have a zero power lens meeting the same requirements as any other A lens. Since the amount of significant additive error remains unchanged in spite of changes in the A lenses, the number of different corrections in all possible lens combinations which must be calculated or are required is reduced by a factor equal to the number of A lenses.

Although the constant radius of the A lenses need not be infinity, a planar surface is preferred since the planar surface reduces the problems associated with constructing a zero power lens (window) to a minimum. The lenses at the reference plane may be made of either glass or plastic since the critical property is index of refraction in the composition of the lens material. As long as all lenses have the same index of refraction, they could even be a mixture of glass and plastic. Also, lenses other than those at the reference plane can be either glass or plastic.

In a refractor having weak sphere lenses, strong sphere lenses, weak cylinder lenses, and strong cylinder lenses, each respectively carried by a rotatable dial to permit a selected one of each group of lenses to be placed before a patient's eye, the preferred embodiment is arranged with the strong sphere dial located at the reference plane and has a series of lenses of identical center thickness, identical glass, and a planar surface on the side of the lenses furthest from the patient's eye. Such a lens series will provide identical error for each combination of cylinder lenses in every position of the strong sphere dial.

The radius of the surface closest to the eye must be individually determined for each lens based upon the spacing of the lens from the eye and the power desired. While not constant, the radii for all lenses in a single dial will be related, since the spacing thickness and index of refraction for all lenses in that dial are identical. The lens series of the present invention when incorporated into a refractor reduces the prior art additive cylinder errors in a refractor having 12 positions of the strong sphere dial by a factor of 12 and provides 100% predictability of the occurrence of significant additive errors since every position of the strong sphere dial has identical errors.

The drawing is an optical diagram illustrating the position of representative lenses in a refractor having a lens series of the present invention.

DETAILED DESCRIPTION OF THE INVENTION AND PREFERRED EMBODIMENT

Referring to FIG. 1, the lenses in the strong sphere disc of a refractor are identified by I and have variable radius $R_{1.1}$ to $R_{1.12}$. The lenses in the weak sphere dial are represented by the lens identified by II and have radii of $R_{2.1}$ to $R_{2.12}$. Similarly, strong cylinder lenses are represented by the lens identified III and have individual radii identified as $R_{3.1}$ to $R_{3.12}$ and weak cylinder lenses represented by the lens identified by IV and have respective radii $R_{4.1}$ to $R_{4.6}$. An auxiliary dial in a refractor is frequently used to carry special optical elements for conducting certain tests during refraction. The optical elements are represented by lens V and preferably include 0.125 diopter auxiliary sphere lens. The lenses have radii $R_{5.1}$ to $R_{5.2}$. Refractors frequently have window VI in order to keep dust and dirt from the interior mechanism and optical surfaces. The distance from the optical surface furthest from the eye of the various elements to the reference plane are identified as D1 to D5 for the weak cylinder lenses, strong cylinder lenses, auxiliary lenses, weak sphere lenses and strong sphere lenses, respectively. The distance from the reference plane to the window and to the patient's eye are respectively identified as D6 and D7. All lenses including the window and auxiliary lens are made of a glass having an index of 1.523, an Abbe number of 58.6 and a thickness of 1.6 millimeters. The index of refraction of the lenses may be varied by $\pm 0.0005$, Abbe number $\pm 0.5$ and thickness (except the auxiliary lens) by $\pm 0.2$ millimter. While zero power position in the weak sphere, strong cylinder, weak cylinder and auxiliary dials is an open aperture, the strong sphere disc has a planar plate of the same glass and thickness as the lenses. This plate has a radius identified as infinity in the table, while zero diopter positions in other discs are noted as having a zero radius since no glass is present.

Since all lenses have an identical center thickness of 1.6 mm, the spacing between lenses of adjacent dials will be identical regardless of which lens in either dial is positioned before the eye. For the lens series of the preferred embodiment S1 is 2.368, S2 is 2.877, S3 is 2.368 and S4 is 2.368 mm. The distances identified in the drawing are D1=17.981, D2=14.013, D3=9.536, D4=5.568, D6=1.6, D6=1.57, and D7=14.27 mm. Table I provides the marked power, real power, calculated radius and actual radius of the variable surface for each lens of respective dials I-IV and the one lens of auxiliary dial V. Those radii, calculated and actual which are 0.00 identify open apertures in the respective discs dials. The lens having radius $R_{3.7}$ has a planar surface on both sides as indicated by the calculated and actual radius of infinity. All the radii are in millimeters and a minus sign (−) denotes a radius having a center on the side of the lens away from the patient's eye.

TABLE I

| POSI-TION | NO. | MARKED POWER | REAL POWER | CALCULATED RADIUS | ACTUAL RADIUS |
|---|---|---|---|---|---|
| STRONG CYLINDRICAL POWERS (DIAL III) | | | | | |
| 1 | $R_{3.1}$ | 0.0 | 0.0 | 0.0 | 0.0 |
| 2 | 3.2 | 0.750 | 0.743 | 703.53797 | 703.538 |
| 3 | 3.3 | 1.500 | 1.474 | 354.87131 | 354.871 |
| 4 | 3.4 | 2.250 | 2.192 | 238.64909 | 238.649 |
| 5 | 3.5 | 3.000 | 2.897 | 180.53797 | 180.538 |
| 6 | 3.6 | 3.750 | 3.590 | 145.67131 | 145.671 |
| 7 | 3.7 | 4.500 | 4.272 | 122.42686 | 122.427 |
| 8 | 3.8 | 5.250 | 4.942 | 105.82369 | 105.824 |
| 9 | 3.9 | 6.000 | 5.601 | 93.37131 | 93.371 |
| 10 | 3.10 | 6.750 | 6.250 | 83.68612 | 83.686 |
| 11 | 3.11 | 7.500 | 6.887 | 75.93797 | 75.938 |
| 12 | 3.12 | 8.250 | 7.515 | 69.59858 | 69.599 |
| WEAK CYLINDRICAL POWERS (DIAL IV) | | | | | |
| 1 | $R_{4.1}$ | 0.0 | 0.0 | 0.0 | 0.0 |
| 2 | 4.2 | 0.125 | 0.125 | 4192.27990 | 4192.280 |
| 3 | 4.3 | 0.250 | 0.249 | 2100.27990 | 2100.280 |
| 4 | 4.4 | 0.375 | 0.373 | 1402.94657 | 1402.947 |
| 5 | 4.5 | 0.500 | 0.496 | 1054.27990 | 1054.280 |
| 6 | 4.6 | 0.625 | 0.619 | 845.07990 | 845.080 |
| STRONG SPHERICAL POWERS (DIAL I) | | | | | |
| 1 | $R_{1.1}$ | −18.000 | −18.000 | −29.05556 | −29.056 |
| 2 | 1.2 | −15.000 | −15.000 | −34.86667 | −34.867 |
| 3 | 1.3 | −12.000 | −12.000 | −43.58333 | −43.583 |
| 4 | 1.4 | −9.000 | −9.000 | −58.11111 | −58.111 |
| 5 | 1.5 | −6.000 | −6.000 | −87.16667 | −67.167 |
| 6 | 1.6 | −3.000 | −3.000 | −174.33333 | −174.333 |
| 7 | 1.7 | 0.0 | 0.000 | ∞ | ∞ |
| 8 | 1.8 | 3.000 | 3.000 | 174.33333 | 174.333 |
| 9 | 1.9 | 6.000 | 6.000 | 87.16667 | 87.167 |
| 10 | 1.10 | 9.000 | 9.000 | 58.11111 | 58.111 |
| 11 | 1.11 | 12.000 | 12.000 | 43.58333 | 43.583 |
| 12 | 1.12 | 15.000 | 15.000 | 34.86667 | 34.867 |
| WEAK SPHERICAL POWERS (DIAL II) | | | | | |
| 1 | $R_{2.1}$ | −1.000 | −1.003 | −521.21209 | −521.212 |
| 2 | 2.2 | −0.750 | −0.752 | −695.54543 | −695.544 |
| 3 | 2.3 | −0.500 | −0.501 | −1044.21209 | −1044.212 |
| 4 | 2.4 | −0.250 | −0.250 | −2090.21209 | −2090.212 |
| 5 | 2.5 | 0.0 | 0.0 | 0.0 | 0.0 |
| 6 | 2.6 | 0.250 | 0.250 | 2093.78791 | 2093.788 |
| 7 | 2.7 | 0.500 | 0.499 | 1047.78791 | 1047.788 |
| 8 | 2.8 | 0.750 | 0.748 | 699.12124 | 699.121 |
| 9 | 2.9 | 1.000 | 0.997 | 524.78791 | 524.788 |
| 10 | 2.10 | 1.250 | 1.245 | 420.18791 | 420.188 |

TABLE I-continued

| POSITION | NO. | MARKED POWER | REAL POWER | CALCULATED RADIUS | ACTUAL RADIUS |
|---|---|---|---|---|---|
| 11 | 2.11 | 1.500 | 1.492 | 350.45457 | 350.455 |
| 12 | 2.12 | 1.750 | 1.740 | 300.64505 | 300.645 |
| AUXILIARY SPHERICAL POWERS (DIAL V) | | | | | |
| 1 | $R_{5.1}$ | 0.0 | 0.0 | 0.0 | 0.0 |
| 2 | 5.2 | 0.125 | 0.125 | 4187.86317 | 4187.86317 |

A refractor having a lens series with the foregoing values will exhibit deviation at far point testing (20 ft.) from the marked additive powers only in those positions shown in Table II. Corrections of +0.125 cylinder diopter for these deviations in marked cylinder power are made by changing the cylinder power for those positions of the weak sphere dial presenting a negative sphere power. For example, when the cylinder power is 8.25; and the weak sphere lens in position 1 of dial II (−1.00 diopter) and auxiliary dial V in position 2 (+0.125 diopter) the correction would be made by increasing the cylinder power from 8.25 to 8.38. Similarly, for those positions of dial II having a spherical power of 0 or greater, the cylinder power would be reduced by 0.125 diopter. For example, when the cylinder power is 6.63, and the weak sphere lens in position 9 of dial II (+1.00 diopter) and auxiliary dial V in position 1 (0.0 diopter) are on the test axis, correction would be made by reducing the cylinder power from 6.63 to 6.50. When the lens combinations for far point testing are adjusted as indicated above, the error for any combination of cylinder and spherical lenses is less than +0.10 cylinder diopters. In fact, for those combinations which have been corrected, the error is reduced to not more than 0.075 diopters. Since the errors occurring in any position of the strong sphere dial I are the same as the errors occurring in any other position of strong sphere dial I, the adjustments which are provided for the zero power position (position 7) of strong sphere dial I are used in all other positions of the strong sphere dial.

TABLE II

| STRONG SPHERE (I) | WEAK SPHERE (II) | AUXILIARY (V) | STRONG CYL. (III) / WEAK CYL. (IV) CYLINDER POWER (DIOPTERS) | | | | | | | | | | | | SPHERE POWER |
|---|---|---|---|---|---|---|---|---|---|---|---|---|---|---|---|
| | | | --01-- 123456 | --02-- 123456 | --03-- 123456 | --04-- 123456 | --05-- 123456 | --06-- 123456 | --07-- 123456 | --08-- 123456 | --09-- 123456 | --10-- 123456 | --11-- 123456 | --12-- 123456 | |
| 7 | 1 | 1 | | | | | | | | | | | | | −1.00 |
| 7 | 1 | 2 | | | | | | | | | | | | | −0.88 |
| 7 | 2 | 1 | | | | | | | | | | | | | −0.75 |
| 7 | 2 | 2 | | | | | | | | | | | | | −0.63 |
| 7 | 3 | 1 | | | | | | | | | | | | | −0.50 |
| 7 | 3 | 2 | | | | | | | | | | | | | −0.38 |
| 7 | 4 | 1 | | | | | | | | | | | | | −0.25 |
| 7 | 4 | 2 | | | | | | | | | | | | | −0.13 |
| 7 | 5 | 1 | | | | | | | | | | | * | * | 0.0 |
| 7 | 5 | 2 | | | | | | | | | | | * | * | 0.13 |
| 7 | 6 | 1 | | | | | | | | | | * | | * | 0.25 |
| 7 | 6 | 2 | | | | | | | | | * | | * | | 0.38 |
| 7 | 7 | 1 | | | | | | | | | * | * | * | * | 0.50 |
| 7 | 7 | 2 | | | | | | | | * | | * | * | *** | 0.63 |
| 7 | 8 | 1 | | | | | | | | * | * | ** | ** | ** | 0.75 |
| 7 | 8 | 2 | | | | | | | * | | * | * | * | * | 0.88 |
| 7 | 9 | 1 | | | | | | | * | * | ** | ** | ** | ** | 1.00 |
| 7 | 9 | 2 | | | | | | | ** | * | * | ** | *** | *** | 1.13 |
| 7 | 10 | 1 | | | | | | * | | ** | * | *** | *** | *** | 1.25 |
| 7 | 10 | 2 | | | | | | ** | * | ** | ** | *** | **** | *** | 1.38 |
| 7 | 11 | 1 | | | | | | * | ** | ** | ** | *** | **** | **** | 1.50 |
| 7 | 11 | 2 | | | | | | | ** | ** | *** | *** | *** | ** | 1.63 |
| 7 | 12 | 1 | | | | | | | ** | ** | *** | *** | **** | **** | 1.75 |
| 7 | 12 | 2 | | | | | | | ** | ** | ** | *** | *** | *** | 1.88 |

FAR POINT ERRORS (BEFORE ADJUSTMENT)

| ERROR RANGE (DIOPTERS) | SYMBOL |
|---|---|
| $E \leq 0.10$ | BLANK |
| $0.10 < E \leq 0.25$ | * |

Table III presents the error range at near point testing (16 in.) for all combinations of the strong cylinder dial III and weak cylinder dial IV with the weak sphere dial II and auxiliary dial V when the strong sphere dial I is in the zero power position (position 7). As can be seen in Table III, the number combinations having error and the amount of error in many combinations is substantially larger than the additive errors encountered during far point testing.

TABLE III

Columns (left to right):
- STRONG SPHERE (I)
- WEAK SPHERE (II)
- AUXILIARY (V)
- STRONG CYL. (III) / WEAK CYL. (III): columns labeled --01-- through --12--, each subdivided 1 2 3 4 5 6
- SPHERE POWER

Row groupings (Strong Sphere = 7 throughout; Weak Sphere, Auxiliary, Sphere Power values):

| Weak Sphere (II) | Auxiliary (V) | Sphere Power |
|---|---|---|
| 1 | 1 | −1.00 |
| 1 | 2 | −0.88 |
| 2 | 1 | −0.75 |
| 2 | 2 | −0.63 |
| 3 | 1 | −0.50 |
| 3 | 2 | −0.38 |
| 4 | 1 | −0.25 |
| 4 | 2 | −0.13 |
| 5 | 1 | 0.0 |
| 5 | 2 | 0.13 |
| 6 | 1 | 0.25 |
| 6 | 2 | 0.38 |
| 7 | 1 | 0.50 |
| 7 | 2 | 0.63 |
| 8 | 1 | 0.75 |
| 8 | 2 | 0.88 |
| 9 | 1 | 1.00 |
| 9 | 2 | 1.13 |
| 10 | 1 | 1.25 |
| 10 | 2 | 1.38 |
| 11 | 1 | 1.50 |
| 11 | 2 | 1.63 |
| 12 | 1 | 1.75 |
| 12 | 2 | 1.88 |

Error range axis (diopters): 0.0 — 1.0 — 2.0 — 3.0 — 4.0 — 5.0 — 6.0 — 7.0 — 8.0 — 9.0

Legend:

| ERROR RANGE (DIOPTERS) | | SYMBOL |
|---|---|---|
| 0.10 | E VII < 0.10 | BLANK |
| 0.25 | E VII < 0.25 | * |
| 0.50 | E VII < 0.50 | # |
| | | x |

Label: NEAR POINT ERRORS (BEFORE ADJUSTMENT)

The body of the table contains a matrix of symbols (blank, *, #, x) plotting error range versus cylinder power for each sphere/auxiliary combination listed above.

After adjustments, the cylinder error can be reduced to less than a tenth of a diopter for all but a few cylinder lens combinations. The cylinder lens combinations after adjustment are shown in Table IV with the range of error associated with each combination. Note that only the very high combinations (over 8.25 diopters of cylinder) result in any error for near point because it is not possible to provide the necessary substantial increases by adjustment since the maximum cylinder power of any combination is 8.75. This explains the substantial cylinder error in the localized region shown by Table IV following adjustment. Table V provides the location and type of cylinder power adjustment required for each combination of cylinder lenses. These adjustment are made for each combination which requires adjustment in the same manner as the adjustments described of negative sphere powers for far point testing.

TABLE IV

| STRONG SPHERE (I) | WEAK SPHERE (II) | AUXILIARY (V) | STRONG CYL. (III) --01-- 123456 | --02-- 123456 | --03-- 123456 | --04-- 123456 | --05-- 123456 | --06-- 123456 WEAK CYL. (IV) | --07-- 123456 | --08-- 123456 | --09-- 123456 | --10-- 123456 | --11-- 123456 | --12-- 123456 | SPHERE POWER |
|---|---|---|---|---|---|---|---|---|---|---|---|---|---|---|---|
| 7 | 1 | 1 | | | | | | | | | | | | x x x x | −1.00 |
| 7 | 1 | 2 | | | | | | | | | | | | x x x x | −0.88 |
| 7 | 2 | 1 | | | | | | | | | | | | #x x x | −0.75 |
| 7 | 2 | 2 | | | | | | | | | | | | #x x x | −0.63 |
| 7 | 3 | 1 | | | | | | | | | | | | * x x x | −0.50 |
| 7 | 3 | 2 | | | | | | | | | | | | * x x x | −0.38 |
| 7 | 4 | 1 | | | | | | | | | | | | x x x | −0.25 |
| 7 | 4 | 2 | | | | | | | | | | | | x x x | −0.13 |
| 7 | 5 | 1 | | | | | | | | | | | | x x x | 0.0 |
| 7 | 5 | 2 | | | | | | | | | | | | x x x | 0.13 |
| 7 | 6 | 1 | | | | | | | | | | | | x x x | 0.25 |
| 7 | 6 | 2 | | | | | | | | | | | | x x x | 0.38 |
| 7 | 7 | 1 | | | | | | | | | | | | x x x | 0.50 |
| 7 | 7 | 2 | | | | | | | | | | | | x x x | 0.63 |
| 7 | 8 | 1 | | | | | | | | | | | | x x x | 0.75 |
| 7 | 8 | 2 | | | | | | | | | | | | x x x | 0.88 |
| 7 | 9 | 1 | | | | | | | | | | | | x x x | 1.00 |
| 7 | 9 | 2 | | | | | | | | | | | | x x x | 1.13 |
| 7 | 10 | 1 | | | | | | | | | | | | x x x | 1.25 |
| 7 | 10 | 2 | | | | | | | | | | | | #x x | 1.38 |
| 7 | 11 | 1 | | | | | | | | | | | | * x x | 1.50 |
| 7 | 11 | 2 | | | | | | | | | | | | * x x | 1.63 |
| 7 | 12 | 1 | | | | | | | | | | | | x x | 1.75 |
| 7 | 12 | 2 | | | | | | | | | | | | x x | 1.88 |

NEAR POINT ERRORS
(BEFORE ADJUSTMENT)

| ERROR RANGE (DIOPTERS) | SYMBOL |
|---|---|
| $E \leq 0.10$ | BLANK |
| $0.1000 < E \leq 0.1125$ | * |
| $0.1125 < E \leq 0.1250$ | # |
| $0.1250 < E$ | x |

TABLE V

| STRONG SPHERE (I) | WEAK SPHERE (II) | AUXILIARY (V) | --01-- 123456 | --02-- 123456 | --03-- 123456 | --04-- 123456 | --05-- 123456 | --06-- WEAK CYL. (IV) 123456 | --07-- 123456 | --08-- 123456 | --09-- 123456 | --10-- 123456 | --11-- 123456 | --12-- 123456 | SPHERE POWER |
|---|---|---|---|---|---|---|---|---|---|---|---|---|---|---|---|
| 7 | 1 | 1 | ...... | ...... | :: 11111 | : 111112 | : 222222 | : 222222 | : 222222 | : 222333 | : 333333 | : 334444 | : 444444 | : 44321 | −1.00 |
| 7 | 1 | 2 | ...... | ...... | :: 1111 | : 111111 | : 122222 | : 222222 | : 222222 | : 333333 | : 333333 | : 334444 | : 444444 | : 44321 | −0.88 |
| 7 | 2 | 1 | ...... | ...... | :: 1111 | : 111112 | : 122222 | : 222222 | : 222222 | : 333333 | : 333433 | : 334444 | : 444444 | : 44321 | −0.75 |
| 7 | 2 | 2 | ...... | ...... | :: 111 | : 111111 | : 111222 | : 222222 | : 222222 | : 323333 | : 333433 | : 334444 | : 444444 | : 44321 | −0.63 |
| 7 | 3 | 1 | ...... | ...... | :: 1111 | : 111111 | : 112222 | : 222222 | : 222333 | : 332333 | : 333333 | : 334444 | : 444444 | : 44321 | −0.50 |
| 7 | 3 | 2 | ...... | ...... | : 111 | : 111111 | : 111112 | : 222222 | : 222333 | : 333333 | : 333333 | : 334444 | : 434444 | : 44321 | −0.38 |
| 7 | 4 | 1 | ...... | ...... | : 111 | : 111111 | : 111112 | : 222222 | : 222333 | : 333333 | : 333333 | : 334444 | : 434444 | : 44321 | −0.25 |
| 7 | 4 | 2 | ...... | ...... | : 11 | : 111111 | : 111112 | : 222222 | : 222333 | : 333333 | : 333333 | : 334444 | : 334444 | : 44321 | −0.13 |
| 7 | 5 | 1 | ...... | ...... | : 111 | : 111111 | : 111112 | : 222222 | : 222333 | : 333333 | : 333333 | : 334433 | : 334444 | : 44321 | 0.0 |
| 7 | 5 | 2 | ...... | ...... | : 11 | : 111111 | : 111112 | : 222222 | : 222333 | : 333333 | : 333333 | : 334433 | : 334444 | : 43321 | 0.13 |
| 7 | 6 | 1 | ...... | ...... | : 11 | : 111111 | : 111112 | : 222222 | : 222222 | : 333333 | : 333333 | : 334433 | : 334444 | : 44321 | 0.25 |
| 7 | 6 | 2 | ...... | ...... | : 1 | : 111111 | : 111112 | : 222222 | : 222222 | : 333333 | : 333333 | : 333433 | : 334444 | : 44321 | 0.38 |
| 7 | 7 | 1 | ...... | ...... | : 111111 | : 111112 | : 222222 | : 222222 | : 333333 | : 333333 | : 333433 | : 333444 | : 44321 | 0.50 |
| 7 | 7 | 2 | ...... | ...... | : 111111 | : 111112 | : 222222 | : 222222 | : 332333 | : 333333 | : 333433 | : 333444 | : 44321 | 0.63 |
| 7 | 8 | 1 | ...... | ...... | : 1 | : 111111 | : 111112 | : 222222 | : 222222 | : 322333 | : 333333 | : 333433 | : 333443 | : 43321 | 0.75 |
| 7 | 8 | 2 | ...... | ...... | : 111111 | : 111112 | : 222222 | : 222222 | : 222333 | : 333333 | : 333443 | : 333443 | : 33321 | 0.88 |
| 7 | 9 | 1 | ...... | ...... | : 111111 | : 111112 | : 221122 | : 222222 | : 222333 | : 333333 | : 333433 | : 333443 | : 33321 | 1.00 |
| 7 | 9 | 2 | ...... | ...... | : 111111 | : 111112 | : 111122 | : 222222 | : 222333 | : 333333 | : 333433 | : 333433 | : 33321 | 1.13 |
| 7 | 10 | 1 | ...... | ...... | : 111111 | : 111111 | : 111122 | : 222222 | : 222333 | : 332333 | : 333333 | : 333433 | : 33321 | 1.25 |
| 7 | 10 | 2 | ...... | ...... | : 111111 | : 111111 | : 111122 | : 222222 | : 222233 | : 322333 | : 333333 | : 333433 | : 33321 | 1.38 |
| 7 | 11 | 1 | ...... | ...... | : 111111 | : 111111 | : 111122 | : 222222 | : 222233 | : 322333 | : 333333 | : 333333 | : 33321 | 1.50 |
| 7 | 11 | 2 | ...... | ...... | : 1111 | : 111111 | : 111122 | : 222122 | : 222233 | : 322333 | : 333333 | : 333333 | : 33321 | 1.63 |
| 7 | 12 | 1 | ...... | ...... | : 11111 | : 111111 | : 111122 | : 222122 | : 222233 | : 322333 | : 333333 | : 333333 | : 33321 | 1.75 |
| 7 | 12 | 2 | ...... | ...... | : 111 | : 111111 | : 111122 | : 222122 | : 222233 | : 322333 | : 333333 | : 333333 | : 33321 | 1.88 |

0.0   1.0   2.0   3.0   4.0   5.0   6.0   7.0   8.0   9.0

NEAR POINT ADJUSTMENTS

| Adjustment Limited By Max. Cylinder Power | ADJUSTMENT | SYMBOL |
|---|---|---|
| | NONE | BLANK |
| | 0.125 | 1 |
| | 0.250 | 2 |
| | 0.375 | 3 |
| | 0.500 | 4 |

Table VI is representative of the amount of cylinder error, at near point, and shows the precise amount of spherical and cylinder error for each combination of the weak cylinder dial IV with the strong cylinder dial III when the spherical power is zero.

Table VII presents the amount of cylinder error for several cylinder powers and varying positions of strong sphere dial I. Note that while the amount of error varies with various cylinder powers, the error remains identical through the entire range from −18 to +15.250 diopters of sphere for that cylinder power so long as the weak sphere dial II and/or auxiliary dial V are not changed.

| DIAL AND POSITION | | | | | MARKED | | ERROR | |
|---|---|---|---|---|---|---|---|---|
| W C | S C | A S | W S | S S | SPHERE | CYL. | SPHERE | CYL. |
| 1 : | 1 : | 1 : | 5 : | 7 | 0.0 | 0.0 | −0.003 | 0.0 |
| 2 : | 1 : | 1 : | 5 : | 7 | 0.0 | 0.125 | −0.007 | −0.010 |
| 3 : | 1 : | 1 : | 5 : | 7 | 0.0 | 0.250 | −0.007 | −0.019 |
| 4 : | 1 : | 1 : | 5 : | 7 | 0.0 | 0.375 | −0.007 | −0.029 |
| 5 : | 1 : | 1 : | 5 : | 7 | 0.0 | 0.500 | −0.007 | −0.038 |
| 6 : | 1 : | 1 : | 5 : | 7 | 0.0 | 0.625 | −0.007 | −0.048 |
| 1 : | 2 : | 1 : | 5 : | 7 | 0.0 | 0.750 | −0.007 | −0.043 |
| 2 : | 2 : | 1 : | 5 : | 7 | 0.0 | 0.875 | −0.010 | −0.051 |
| 3 : | 2 : | 1 : | 5 : | 7 | 0.0 | 1.000 | −0.010 | −0.058 |
| 4 : | 2 : | 1 : | 5 : | 7 | 0.0 | 1.125 | −0.010 | −0.065 |
| 5 : | 2 : | 1 : | 5 : | 7 | 0.0 | 1.250 | −0.010 | −0.073 |
| 6 : | 2 : | 1 : | 5 : | 7 | 0.0 | 1.375 | −0.010 | −0.080 |
| 1 : | 3 : | 1 : | 5 : | 7 | 0.0 | 1.500 | −0.007 | −0.087 |
| 2 : | 3 : | 1 : | 5 : | 7 | 0.0 | 1.625 | −0.010 | −0.093 |
| 3 : | 3 : | 1 : | 5 : | 7 | 0.0 | 1.750 | −0.010 | −0.098 |
| 4 : | 3 : | 1 : | 5 : | 7 | 0.0 | 1.875 | −0.010 | −0.103 |
| 5 : | 3 : | 1 : | 5 : | 7 | 0.0 | 2.000 | −0.010 | −0.109 |
| 6 : | 3 : | 1 : | 5 : | 7 | 0.0 | 2.125 | −0.010 | −0.114 |
| 1 : | 4 : | 1 : | 5 : | 7 | 0.0 | 2.250 | −0.007 | −0.131 |
| 2 : | 4 : | 1 : | 5 : | 7 | 0.0 | 2.375 | −0.010 | −0.135 |
| 3 : | 4 : | 1 : | 5 : | 7 | 0.0 | 2.500 | −0.010 | −0.138 |
| 4 : | 4 : | 1 : | 5 : | 7 | 0.0 | 2.625 | −0.010 | −0.141 |
| 5 : | 4 : | 1 : | 5 : | 7 | 0.0 | 2.750 | −0.010 | −0.145 |
| 6 : | 4 : | 1 : | 5 : | 7 | 0.0 | 2.875 | −0.010 | −0.148 |
| 1 : | 5 : | 1 : | 5 : | 7 | 0.0 | 3.000 | −0.007 | −0.176 |
| 2 : | 5 : | 1 : | 5 : | 7 | 0.0 | 3.125 | −0.010 | −0.177 |
| 3 : | 5 : | 1 : | 5 : | 7 | 0.0 | 3.250 | −0.010 | −0.179 |
| 4 : | 5 : | 1 : | 5 : | 7 | 0.0 | 3.375 | −0.010 | −0.180 |
| 5 : | 5 : | 1 : | 5 : | 7 | 0.0 | 3.500 | −0.010 | −0.181 |
| 6 : | 5 : | 1 : | 5 : | 7 | 0.0 | 3.625 | −0.010 | −0.182 |
| 1 : | 6 : | 1 : | 5 : | 7 | 0.0 | 3.750 | −0.007 | −0.221 |
| 2 : | 6 : | 1 : | 5 : | 7 | 0.0 | 3.875 | −0.010 | −0.220 |
| 3 : | 6 : | 1 : | 5 : | 7 | 0.0 | 4.000 | −0.010 | −0.219 |
| 4 : | 6 : | 1 : | 5 : | 7 | 0.0 | 4.125 | −0.010 | −0.218 |
| 5 : | 6 : | 1 : | 5 : | 7 | 0.0 | 4.250 | −0.010 | −0.218 |
| 6 : | 6 : | 1 : | 5 : | 7 | 0.0 | 4.375 | −0.010 | −0.217 |
| 1 : | 7 : | 1 : | 5 : | 7 | 0.0 | 4.500 | −0.007 | −0.266 |
| 2 : | 7 : | 1 : | 5 : | 7 | 0.0 | 4.625 | −0.010 | −0.264 |
| 3 : | 7 : | 1 : | 5 : | 7 | 0.0 | 4.750 | −0.010 | −0.261 |
| 4 : | 7 : | 1 : | 5 : | 7 | 0.0 | 4.875 | −0.010 | −0.258 |
| 5 : | 7 : | 1 : | 5 : | 7 | 0.0 | 5.000 | −0.010 | −0.255 |
| 6 : | 7 : | 1 : | 5 : | 7 | 0.0 | 5.125 | −0.010 | −0.252 |
| 1 : | 8 : | 1 : | 5 : | 7 | 0.0 | 5.250 | −0.007 | −0.312 |
| 2 : | 8 : | 1 : | 5 : | 7 | 0.0 | 5.375 | −0.010 | −0.307 |
| 3 : | 8 : | 1 : | 5 : | 7 | 0.0 | 5.500 | −0.010 | −0.302 |
| 4 : | 8 : | 1 : | 5 : | 7 | 0.0 | 5.625 | −0.010 | −0.297 |
| 5 : | 8 : | 1 : | 5 : | 7 | 0.0 | 5.750 | −0.010 | −0.292 |
| 6 : | 8 : | 1 : | 5 : | 7 | 0.0 | 5.875 | −0.010 | −0.287 |
| 1 : | 9 : | 1 : | 5 : | 7 | 0.0 | 6.000 | −0.007 | −0.358 |
| 2 : | 9 : | 1 : | 5 : | 7 | 0.0 | 6.125 | −0.010 | −0.351 |
| 3 : | 9 : | 1 : | 5 : | 7 | 0.0 | 6.250 | −0.010 | −0.344 |
| 4 : | 9 : | 1 : | 5 : | 7 | 0.0 | 6.375 | −0.010 | −0.337 |
| 5 : | 9 : | 1 : | 5 : | 7 | 0.0 | 6.500 | −0.010 | −0.329 |
| 6 : | 9 : | 1 : | 5 : | 7 | 0.0 | 6.625 | −0.010 | −0.322 |
| 1 : | 10 : | 1 : | 5 : | 7 | 0.0 | 6.750 | −0.007 | −0.404 |
| 2 : | 10 : | 1 : | 5 : | 7 | 0.0 | 6.875 | −0.010 | −0.395 |
| 3 : | 10 : | 1 : | 5 : | 7 | 0.0 | 7.000 | −0.010 | −0.386 |
| 4 : | 10 : | 1 : | 5 : | 7 | 0.0 | 7.125 | −0.010 | −0.377 |
| 5 : | 10 : | 1 : | 5 : | 7 | 0.0 | 7.250 | −0.010 | −0.367 |
| 6 : | 10 : | 1 : | 5 : | 7 | 0.0 | 7.375 | −0.010 | −0.385 |
| 1 : | 11 : | 1 : | 5 : | 7 | 0.0 | 7.500 | −0.007 | −0.451 |
| 2 : | 11 : | 1 : | 5 : | 7 | 0.0 | 7.625 | −0.010 | −0.440 |
| 3 : | 11 : | 1 : | 5 : | 7 | 0.0 | 7.750 | −0.010 | −0.429 |
| 4 : | 11 : | 1 : | 5 : | 7 | 0.0 | 7.875 | −0.010 | −0.417 |
| 5 : | 11 : | 1 : | 5 : | 7 | 0.0 | 8.000 | −0.010 | −0.405 |
| 6 : | 11 : | 1 : | 5 : | 7 | 0.0 | 8.125 | −0.010 | −0.394 |
| 1 : | 12 : | 1 : | 5 : | 7 | 0.0 | 8.250 | −0.007 | −0.498 |
| 2 : | 12 : | 1 : | 5 : | 7 | 0.0 | 8.375 | −0.010 | −0.485 |
| 3 : | 12 : | 1 : | 5 : | 7 | 0.0 | 8.500 | −0.010 | −0.471 |
| 4 : | 12 : | 1 : | 5 : | 7 | 0.0 | 8.625 | −0.010 | −0.458 |

-continued

| DIAL AND POSITION | | | | | MARKED | | ERROR | |
|---|---|---|---|---|---|---|---|---|
| WC | SC | AS | WS | SS | SPHERE | CYL. | SPHERE | CYL. |
| 5 : | 12 : | 1 : | 5 : | 7 | 0.0 | 8.750 | −0.010 | −0.444 |
| 6 : | 12 : | 1 : | 5 : | 7 | 0.0 | 8.875 | −0.010 | −0.430 |
| IV | III | V | II | I | | | | |
| 1 : | 9 : | 1 : | 6 : | 1 | −17.750 | 6.000 | | −0.350 |
| 1 : | 9 : | 1 : | 6 : | 4 | −8.750 | 6.000 | | −0.350 |
| 1 : | 9 : | 1 : | 6 : | 7 | 0.250 | 6.000 | | −0.350 |
| 1 : | 9 : | 1 : | 6 : | 10 | 9.250 | 6.000 | | −0.350 |
| 1 : | 9 : | 1 : | 6 : | 12 | 15.250 | 6.000 | | −0.350 |
| 1 : | 9 : | 1 : | 5 : | 1 | −18.000 | 6.000 | | −0.358 |
| 1 : | 9 : | 1 : | 5 : | 4 | −9.000 | 6.000 | | −0.358 |
| 1 : | 9 : | 1 : | 5 : | 7 | 0.000 | 6.000 | | −0.358 |
| 1 : | 9 : | 1 : | 5 : | 10 | 9.000 | 6.000 | | −0.358 |
| 1 : | 9 : | 1 : | 5 : | 12 | 15.000 | 6.000 | | −0.358 |
| 5 : | 11 : | 1 : | 5 : | 1 | −18.000 | 8.000 | | −0.405 |
| 5 : | 11 : | 1 : | 5 : | 4 | −9.000 | 8.000 | | −0.405 |
| 5 : | 11 : | 1 : | 5 : | 7 | 0.000 | 8.000 | | −0.405 |
| 5 : | 11 : | 1 : | 5 : | 10 | 9.000 | 8.000 | | −0.405 |
| 5 : | 11 : | 1 : | 5 : | 12 | 15.000 | 8.000 | | −0.405 |
| 6 : | 12 : | 1 : | 5 : | 1 | −18.000 | 8.875 | | −0.430 |
| 6 : | 12 : | 1 : | 5 : | 4 | −9.000 | 8.875 | | −0.430 |
| 6 : | 12 : | 1 : | 5 : | 7 | 0.000 | 8.875 | | −0.430 |
| 6 : | 12 : | 1 : | 5 : | 10 | 9.000 | 8.875 | | −0.430 |
| 6 : | 12 : | 1 : | 5 : | 12 | 15.000 | 8.875 | | −0.430 |

Obviously, if one elected to place the strong cylinder lenses in the dial positioned at the referenced plane (A lenses) then the additive error of the system would be spherical and cylinder powers would not require correction.

Since only two charts, one for distance and one for near, would be required to identify the positions and the amount of adjustment required for a refractor having a lens series according to the present invention, it would be possible for the practitioner to refer to the chart and manually make the adjustment. However, because the combination of lenses having refractive errors is now 100% predictable, large computers (micro computer and the like) or programmable desk calculating machines are no longer necessary to correct for additive error. In fact, it is now feasible to utilize a microprocessor since the positions requiring correction have been reduced by factor of 12 according to the preferred embodiment.

Refractors commonly have gear means for rotating all cylinder lenses, whether on the test axis or not, during examination. It may be convenient to mold the peripheral gear conventionally used as an integral part of each cylinder lens. This may be conveniently accomplished by using a polycarbonate resin. The following table sets forth the calculating radii for cylinder lenses (dials III and IV) molded of a polycarbonate resin having an index of refraction of 1.5842.

TABLE I

| POSITION | NO. | MARKED POWER | CALCULATED RADIUS |
|---|---|---|---|
| STRONG CYLINDRICAL POWERS (DIAL III) | | | |
| 1 | $R_{3.1}$ | 0.0 | 0.0 |
| 2 | 3.2 | 0.750 | 785.86402 |
| 3 | 3.3 | 1.500 | 396.39736 |
| 4 | 3.4 | 2.250 | 266.57514 |
| 5 | 3.5 | 3.000 | 201.66402 |
| 6 | 3.6 | 3.750 | 162.71736 |
| 7 | 3.7 | 4.500 | 136.75291 |
| 8 | 3.8 | 5.250 | 118.20688 |
| 9 | 3.9 | 6.000 | 104.29736 |
| 10 | 3.10 | 6.750 | 93.47884 |
| 11 | 3.11 | 7.500 | 84.82402 |
| 12 | 3.12 | 8.250 | 77.74281 |
| WEAK CYLINDRICAL POWERS (DIAL IV) | | | |
| 1 | $R_{4.1}$ | 0.0 | 0.0 |
| 2 | 4.2 | 0.125 | 4682.84879 |
| 3 | 4.3 | 0.250 | 2346.04879 |
| 4 | 4.4 | 0.375 | 1567.11546 |
| 5 | 4.5 | 0.500 | 1177.64879 |
| 6 | 4.6 | 0.625 | 943.96879 |

What is claimed is:

1. A lens series for a refractor having a plurality of lenses positionable at each of more than two positions spaced along an optical axis and a reference plane at one of the positions which comprises, the plurality of lenses being positionable at the reference plane including a zero power lens having the same index of refraction, having the same thickness, having the same radius on one surface and the same distance to other lenses on the optical axis.

2. A lens series according to claim 1 wherein at least some of the lenses are plastic.

3. The lens series of claim 2 wherein the plastic is polycarbonate.

* * * * *